US006296767B1

United States Patent
Shaw et al.

(10) Patent No.: US 6,296,767 B1
(45) Date of Patent: Oct. 2, 2001

(54) METHOD AND APPARATUS FOR DIFFUSIVE TRANSFER BETWEEN IMMISCIBLE FLUIDS

(75) Inventors: John Edward Andrew Shaw, West Drayton; Anthony Robert Corless, Ash; Michael Jonathan Harper, London, all of (GB)

(73) Assignee: British Nuclear Fuels plc, Cheshire (GB)

( * ) Notice: Subject to any disclaimer, the term of this patent is extended or adjusted under 35 U.S.C. 154(b) by 0 days.

(21) Appl. No.: 09/171,448

(22) PCT Filed: Apr. 15, 1997

(86) PCT No.: PCT/GB97/01029

§ 371 Date: Apr. 29, 1999

§ 102(e) Date: Apr. 29, 1999

(87) PCT Pub. No.: WO97/39815

PCT Pub. Date: Oct. 30, 1997

(30) Foreign Application Priority Data

Apr. 19, 1996 (GB) .................................................. 9608123
Apr. 19, 1996 (GB) .................................................. 9608124

(51) Int. Cl.[7] .................................................. B01D 11/00
(52) U.S. Cl. .............................. 210/634; 216/2; 210/511; 210/767; 422/68.1
(58) Field of Search ................................. 210/137, 243, 210/321.84, 321.85, 511, 634, 644, 748, 767; 209/1, 155; 422/68.1; 436/180; 216/2, 56

(56) References Cited

U.S. PATENT DOCUMENTS

| 4,214,981 | * | 7/1980 | Giddings | 209/155 |
| 4,789,468 | * | 12/1988 | Sirkar | 210/137 |
| 5,193,688 | * | 3/1993 | Giddings | 210/748 |
| 5,252,220 | * | 10/1993 | Coughlin et al. | 210/644 |
| 5,304,487 | * | 4/1994 | Wilding et al. | 210/634 |
| 5,437,799 | * | 8/1995 | Kissler et al. | 210/511 |
| 5,932,100 | * | 8/1999 | Yager et al. | 210/511 |

FOREIGN PATENT DOCUMENTS

WO 96/12540   5/1996   (WO).
WO 96/12541   5/1996   (WO).

* cited by examiner

Primary Examiner—Joseph W. Drodge
(74) Attorney, Agent, or Firm—Crowell & Moring LLP

(57) ABSTRACT

Apparatus for carrying out a process between first and second immiscible fluids, comprises first and second channels defining flow paths, for permitting fluid flow of respective first and second immiscible fluids therethrough. Portions of the flow paths are disposed close to, or adjacent to, one another and communicate with one another to define a region in which, in use, a stable interface between the fluids is formed. One, or more, dimensions of the region are varied along the length of the interface in a direction of fluid flow to compensate for variation in the properties of the fluids during the carrying out of the process and thereby maintain stability of the interface.

18 Claims, 2 Drawing Sheets

METHOD AND APPARATUS FOR DIFFUSIVE TRANSFER BETWEEN IMMISCIBLE FLUIDS

This application is a 371 of application PCT/GB97/01029, filed on Apr 15, 1997.

FIELD OF THE INVENTION

The present invention relates to a method and apparatus for carrying out a process between first and second inmmiscible fluids, for example solvent extraction from one fluid to another.

BACKGROUND ART

In the chemical industry a common technique for purifying or analysing chemicals is an exchange process. Solvent extraction relies upon the preferential transfer of one or more components from one phase (fluid) in which the component (solute) is dissolved into a second immiscible phase. Usually this is accomplished by physical mixing followed by separation of the two phases using gravity. It has been found that the more thoroughly the two phases are mixed, the more rapidly the transfer process proceeds by reason of the greater surface area of the smaller globules of liquid and reduced diffusion distances within the phases. The time for separation of the phases however increases with more thorough mixing, and hence for a desired efficiency of solute transfer, the separation time may become unacceptably long, this being the principal disadvantage of the process.

Our copending International Application PCT/GB95/02489 discloses a method and means of bringing first and second immiscible fluids in contact with one another for interaction, while inhibiting physical mixing of the fluids, to permit easy separation of the fluids subsequent to interaction, and claims apparatus for carrying out a process between first and second immiscible fluids, the apparatus comprising first and second flow paths for permitting fluid flow of respective first and second immiscible fluids therethrough, portions of the flow paths being disposed close to or adjacent one another and communicating with one another in a region which is such as to permit the fluids to form a stable open interface therein, and wherein at least the first flow path in the interface region has a width normal to the interface within the range 10 to 500 μm.

The Application also discloses a method of carrying out a process between first and second immiscible fluids, the method comprising:

1) providing first and second flow paths having portions disposed adjacent to or close to one another and communicating with one another in a region in which the fluids can contact one another;
2) flowing the first and second immiscible fluids through respective said first and second flow paths such that, at least in said region, the flow of both fluids is essentially laminar, and a stable open interface is formed between the fluids;
3) permitting significant transfer of a desired entity at said interface between the fluids by diffusive transport within the fluids; and
4) flowing the fluids away from the interface region in their respective flow paths without mixing of the fluids.

In the interface region, the flow paths are close to or adjacent one another so that fluid flow through the flow paths continually replenishes the fluid at the interface.

An object of the present invention is to provide a means of stabilising the interface between the liquids It has now been realised that, although the liquids contact one another for a relatively short time and over a relatively short interface length, nevertheless the properties such as density, viscosity, inter-facial tension and volumes of the two liquids may vary across the interface length in consequence of the continuous transfer of a solute, for example, and this may disturb the operation of transfer unless some means for compensation is provided.

An object of the present invention is to provide a means of compensating for the aforementioned disturbance of the diffusive transfer across the interface The present invention is applicable to the formation of an open interface maintained by surface tension, or to an interface maintained by a porous membrane between the fluids, as for example described in our copending International Application PCT/GB95/02488.

According to one aspect of the present invention there is provided an apparatus for carrying out a process between first and second immiscible fluids, the apparatus comprising first and second channels defining flow paths for permitting fluid flow of respective first and second immiscible fluids therethrough, portions of the flow paths being disposed close to, or adjacent to, one another and communicating with one another to define a region in which, in use, a stable interface between the fluids is formed, further characterised in that one or more dimensions of the region is varied along the length of the interface in a direction of fluid flow to compensate for variation in the properties of the fluids during the carrying out of the process and thereby maintain stability of the interface.

The cross sectional area of at least the first flow path is changed and preferably the cross sectional area of at least the second flow path is also changed.

In the case of an apparatus having, an open interface formed between the flow paths,it is preferable that the height of the interface is varied along the length of the interface in the direction of fluid flow.

In the case where the interface is defined by a porous or foraminated sheet the dimensions of the apertures in the sheet are varied along the length of the interface.

Preferably, at least at said region where the interface is formed, the first and second channels merge to form one or more tubes, the, or each of which, has two walls which converge in a direction extending normal to the interface to define a tapering cross section extending in a direction away from the open interface to hold or trap the fluid therein.

Preferably the channels merge at said region to form a tube of triangular cross sectional shape, with one apex of the triangle defining the first fluid flow path and a base of the triangular shape defining the second flow path.

Alternatively the channels merge at said region to form a tube having a cross sectional shape comprising a plurality of pairs of walls which converge mutually in a direction extending radially outwards relative to a central axis of the tube to form an apex, said apices defining the first fluid flow paths and the second flow paths being formed by a void extending along said central axis of the tube. The tube may be of star shaped cross section.

According to another aspect of the present invention there is provided a method of carrying out a process between first and second immiscible fluids, the apparatus comprising first and second channels defining flow paths for permitting fluid flow of respective first and second immiscible fluids therethrough, portions of the flow paths being disposed close to, or adjacent to, one another and communicating with one another to define a region in which, in use, a stable interface between the fluids is formed, further characterised in that one or more dimensions of the region is varied along the length of the interface in a direction of fluid flow to compensate for variation in the properties of the fluids during the carrying out of the process and thereby maintain stability of the interface.

As described in our copending International Applications PCT/GB95/02489, and PCT/GB95/02488, the interface position may be set and stabilised at a narrowing in the opening between channels or pores. The height d of the narrow part of the opening affects the pressure difference which may be maintained between immiscible fluids across the interface. Generally the maximum pressure differential for stability is described by an expression of the form $$(P_1-P_2) < (2\gamma \cdot \cos\theta)/d$$

where $P_1$, and $P_2$ are pressures in the immiscible fluids 1 and 2 either side of the interface, y is the interfacial tension, and $\theta$ is the value of an angle containing the contact angle between the interface and wall material, and an angle between the wall and plane of the opening.

The carrying out of the process may also result in changes of surface tension properties of the fluids. Thus there may be a net reduction in the surface tension between the fluids, whence a reduction of the height of the open interface (or a reduction in pore cross-section where an intervening membrane is employed) may be necessary. Conversely where a net increase in the interfacial surface tension occurs, an increase in opening height (or pore cross-section) may be allowed which will enhance material transfer.

When operating a stable open interface between immiscible fluids flowing in contacting flow paths it is necessary to limit the pressure differentials existing at all points along the interface to values compatible with the interface height, wall to interface contact angles, and the inter-fluid interfacial tension as set forth in International Application PCT/GB95/02489. It is not necessary nor in general desirable that the pressure differential across the interface is zero, but it must be maintained within bounds set by device geometry and material characteristics. During material transfer in the interface region the amounts of material within each phase changes and correspondingly the material properties such as density, viscosity, and interfacial tension will change. This will cause the rate of pressure drop along each contacting channel containing immiscible fluids to vary differently. The ability of a pinned interface to deform and to accommodate a range of pressure differentials, allows stable flow without break up of the interface to occur; this is provided that the differences in pressure drop variation are not so great as to produce excessive pressure differentials across the interface at any point within the contactor. However where enough material transfer between fluids occurs to modify fluid volumes and material properties sufficiently, and the channel cross section, interface height, and total mass flow rates remain fixed, it is clear that conditions leading to interface, and hence contactor, instability can occur. Sufficiently reducing total mass flow rates can arrest the onset of instability, but reduction in throughput is undesirable. In accordance with the invention, the flow path and/or contact region geometry along the contactor are varied to accommodate the changes in fluid volumes, viscosities, and interfacial tensions which occur along the contactor.

Total mass flow rates for contacting channels must be equal over any contacting length, but where material transfer between the immiscible fluids changes the fluid density, then both individual channel volumetric flow rates, and the total volumetric flow rates for contacting channels, will change over the contacting length. In order to maintain stability, it is desirable that the rate of pressure drop within the contacting channels be maintained nearly equal by widening or narrowing channels to accommodate the changes in volumetric flow rate and viscosity due to changes in fluid composition. Alternately, or additionally, the height of the contacting interface may be changed along the contactor to accommodate changes in the pressure differential produced across the interface along the channel contact region. The desired changes in device geometry for a particular inter-fluid exchange system may be determined experimentally, or may be calculated where sufficient information exists on the system.

A means of maintaining interface stability while allowing movement of the interface to accomodate changes in fluid volumes and properties resulting from contact of the fluids and material transfer between fluids, is provided by forming the interface in structures where walls defining the end of the interface approach one another at an angle. In accordance with the present invention under appropriate conditions, it is possible to stabilise the interface by defining one flow path as tapering away in cross section from the open interface so that the containing walls close together and effectively hold or trap the fluid which preferably wets the wall materials in the tapered region; in such an arrangement it is not necessary to provide a discontinuity between the two flow paths. Thus in one preferred form, the first and second flow paths are defined by a simple tube of triangular cross-section, with one flow path being located in the region of one apex of the triangle. Flow paths for the fluid preferentially wetting the wall materials may be established in each apex of the triangle or apices of other channel cross-section with well defined apices such as diamond or star shapes. It is not neccessary that such cross sections are symetrical. A series of such apices may be formed as part of grooves or channels etched or otherwise formed in a the surface of a plate or other solid body. Channels to carry the immiscible fluids may be formed by holding or bonding together such bodies with other such formed bodies or with bodies having plane surfaces.

Connections to the flow paths within the apices may be established using finer channels or pores such that the fluid which does not preferentially wet the wall materials is prevented by surface tension effects from entering those finer channels or pores.

Thus, the present invention provides apparatus for carrying out a process between first and second immiscible fluids, the apparatus comprising first and second flow paths for permitting fluid flow of respective first and second immiscible fluids there through, portions of the flow paths being disposed close to or adjacent one another and communicating with one another in a region which is such as to permit the fluids to form a stable interface therein, and wherein at least one flow path tapers away in cross section from the open interface such that containing walls hold or trap the fluid therein.

BRIEF DESCRIPTION OF THE DRAWINGS

Preferred embodiments of the invention will now be described with reference to the accompanying drawings, in which.

DESCRIPTION OF THE PREFERRED EMBODIMENTS

Figure 1:
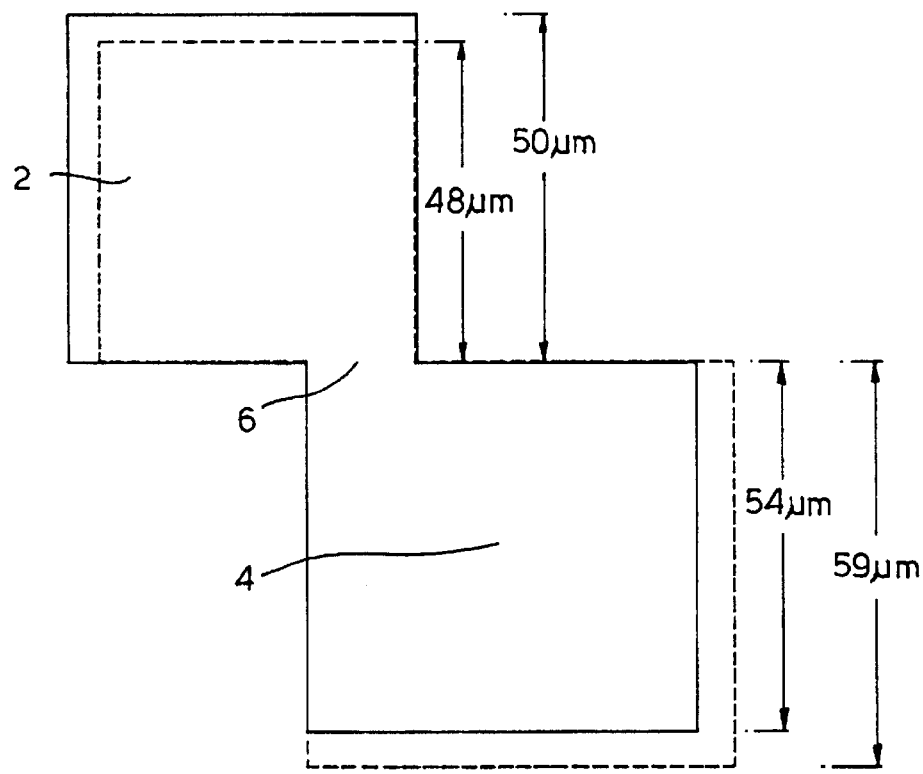
FIG. 1 is a cross-sectional view of apparatus according to a first embodiment wherein the dimensions of the flow paths is gradually changed.

Referring to FIG. 1, a channel of rectangular cross-section, 50×50 $\mu$m defines a first flow path 2 carrying a first liquid such as, for example, an aqueous nitric acid solvent in which is dissolved, in a ⅔ molar solution, hexavalent uranium (ie. the first liquid is $UO_2(NO_3)_2$). A second channel 4 of rectangular cross-section, 54×54 $\mu$m defines a second flow path 4 carrying, for example, an organic liquid consisting of a 20% solution tri-n-butyl phosphate (herein referred to as "tbp") in kerosene. Both liquids flow at the rate of one millilitre per day.

An interface 6 is generated between the two flow paths 2, 4. The interface is 20 $\mu$m wide and extends for a length of 3 cm in the direction of flow along the channels. Transfer of uranium and nitric acid between the fluids is achieved at the interface 6 by diffusive transfer; (the uranium forms a complex with the tbp). The uranium is subsequently separated from the tbp by a similar process in a separate apparatus. At the interface 6, the compositions of the fluids approach their equilibrium values governed by partition coefficients for the materials constituents of the fluids. The table below show changes in fluid composition, volume, density and viscosity which occur as material transfer between the fluids approaches equilibrium. The table also shows changes in channel dimensions, calculated in accordance with the present invention, necessary to maintain near zero change in the pressure differential across the interface whilst maintaining the input mass flows and pressure gradients along the lengths of the channels.

The table below shows that for this particular example, maintenance of stability is enhanced where, in accordance with the present invention, the dimensions of the sides of the channel 2 (flow path 2) changes over the length of the interface from 50 to about 48 $\mu$m, and the sides of channel 4 (flow path 4) changes from 54 to 59 $\mu$m.

In the table below the aqueous liquid was fed in at the rate of 1 cc/24 hrs and had a viscosity of 1.40 centipoise. The organic liquid was fed in at the rate of 1 cc/24 hrs and had a viscosity of 1.96 centipoise. The pressure (dp/dl) along the interface was 73800N/m³.

| Aq in $U_6$ nitrate moles/l | Aq in + $HNO_3$ moles/l | Org in $U_6$ + moles/l | Org in $HNO_3$ moles/l | Density Aq in g/cc | Aq in $UO_2$ $(NO_3)_2$ g/l | Aq in $HNO_3$ g/l | Aq in $H_2O$ g/l | Ratio in Org/Aq vol flows | Density Org in g/cc | Org in $UO_2$ $(NO_3)_2$ g/ Ratio*1 | Org in $HNO_3$ g/ Ratio*1 | Org in TBP/Solvent g/ Ratio*1 |
|---|---|---|---|---|---|---|---|---|---|---|---|---|
| 0.67 | 5 | 0 | 0 | 1.37 | 264 | 315 | 795 | 1 | 0.82 | 0 | 0 | 816 |
| Transfer $UO_2$ $(NO_3)_2$ g | Transfer $HNO_3$ g | New Aq $UO_2$ $(NO_3)_2$ g | New Aq $HNO_3$ g | New Aq $H_2O$ g | New Aq total g | New Org $UO_2$ $(NO_3)_2$ | New Org $HNO_3$ | New Org TBP/ Solv. | New Org total | New Aq Density g/cc | New Org Density g/cc |
| 135 | 10 | 129 | 305 | 795 | 1230 | 135 | 10 | 816 | 961 | 1.27 | 0.93 |
| New Aq U moles/l | New Aq H+ moles/l | New Org U moles/l | New Org H+ moles/l | New Aq Visc. cpoise | New Org Visc. cpoise | New Aq Volume litres | New Org Volume litres | Vol. Flow ratio New Aq/ Old Aq | Vol. Flow Ratio New Org/ Old Org | New Aq vol flow cc/24 h | New Org vol flow cc/24 h |
| 0.34 | 4.99 | 0.33 | 0.15 | 1.19 | 2.65 | 0.97 | 1.04 | 0.97 | 1.04 | 0.97 | 1.04 |
| Original side sq. dP/dl N/m³ | | | | of side sq for new aq micron | | | | of for new org micron | | | |
| 73800 | | | | 48 | | | | 59 | | | |

In a modification, where the pressure gradient is allowed to change along the flow path, and the dimensions of channel 2 are maintained constant, but the dimensions of flow path 4 are varied, the change of pressure differential between flows is minimised to maintain stability by changing the height of the sides of channel 4 (flow path 4) from 54 $\mu$m to 61 $\mu$m.

Where contact time is sufficiently limited for material transfer to be incomplete, the changes in volume, density and viscosity will be more limited but may be calculated in a similar fashion or determined experimentally, and the dimensional changes for those conditions applied in the design of contactor apparatus according to the present invention. A profile of preferred dimensional change through a contactor may be obtained. For the case shown above, the channels are taken as being of square cross section, but may be of alternative cross sectional shape, such as may be conveniently produced by a variety of fabrication techniques. For example the cross sectional shape may be a D or V shape, formed by etching flat Silicon or glass substrates. The calculations of the desired variation may be more complex with channels of different cross sectional shapes but may be achieved using well established physical relationships governing fluid flow.

As regards interfacial tension during mass transfer, changes may occur as systems progress towards equilibrium and the interface concentrations of the transferring species and surface active extractants change, since the surface activity of products such as metal-extractant complexes will be different from those of the simple extractant molecules.

Figure 2:
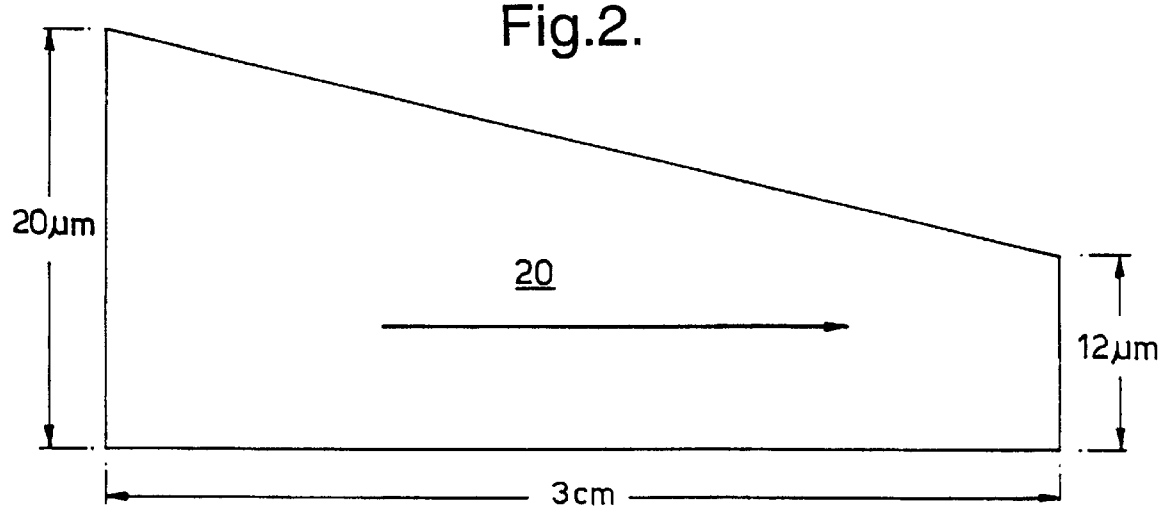
FIG. 2 is a sectional view of a further embodiment showing a gradual decrease in interface height over the length of an interface.

The interface concentration of the surface active transferring species or extractant ligands, (or both in some cases), will reflect effects of both diffusion coefficients and the prevailing diffusion geometry. The interfacial tension affects directly the values of interfacial pressure which may be sustained with a pinned interface, and thereby the contactor stability. Generally, the greater the interfacial tension ($\gamma$), the greater will be the pressure differential ($\Delta P$) which can be sustained at an opening. The maximum opening size may be related to the radius (r) of curvature of an interface given by:

$$\Delta P = \gamma/r$$

and will not be less than twice that radius for a stable system. This maximum is further modified by effects relating to contact angles as described in our copending International Application PCT/GB95/02489. It will usually be necessary to select values and range of openings and their variation on the basis of experiment. As an example, the interfacial tension between a $10^{-5}$ molar aqueous solution of hexanoic acid and hexane has been measured to be ~40 dyne/cm whilst transfer is progressing under semi-infinite diffusion conditions, but ~25 dyne/cm where aqueous and organic solutions have been equilibrated. In order that the same interfacial pressure be sustainable for $\gamma \pm 25$ dyne/cm, as for $\gamma = 40$ dyne/cm, a decrease of opening size is required. For the case where the initial value of the opening close to the original inter-fluid contact is selected as 20 $\mu$m on the basis described in the earlier patents, the order of desired reduction will be from 20 $\mu$m to 12 $\mu$m. This is shown schematically in FIG. 2 wherein the height of an interface region 20 between two fluid flow paths changes from 20 micrometres to 12 micrometres over its length. The height of the region may vary linearly as shown or non-linearly.

Figure 3:
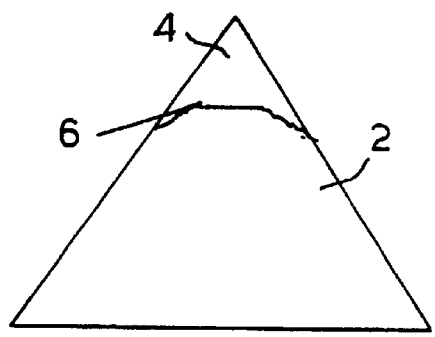
FIG. 3 is a cross-sectional view of a third embodiment of apparatus according to the invention in an interface region.

Referring to FIG. 3 there is shown a cross-sectional view of a channel 2 in the form of a triangle of equilateral form, wherein a first fluid phase preferably wetting the wall material is held in an apex region 4; apex region 4 thus defines a first fluid flow path. A second fluid phase immiscible with the first fluid fills the remainder of the channel, which accordingly defines a second fluid flow path. An interface 6 is defined between the fluids, across which a desired diffusion of a solute from one fluid to the other may occur.

The interface is stable for appropriate conditions of flow and pressure for the fluids concerned.

Figure 4:
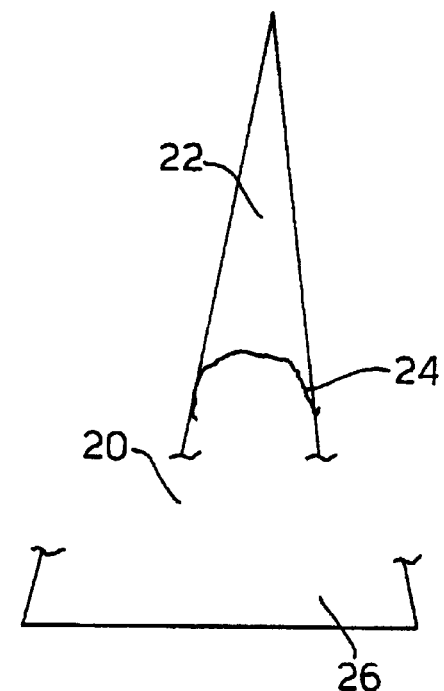
FIG. 4 is a view of a fourth embodiment of the present invention corresponding to that of FIG. 3.

Referring to FIG. 4, there is shown a modification of the embodiment of FIG. 3, where one apex 20 of a channel 22 triangular in section, subtends a very narrow angle, for example 7°. This provides improved conditions for stability of the first fluid flow path and the open interface 24 between the two fluid flow paths 20,26.

Figure 5:
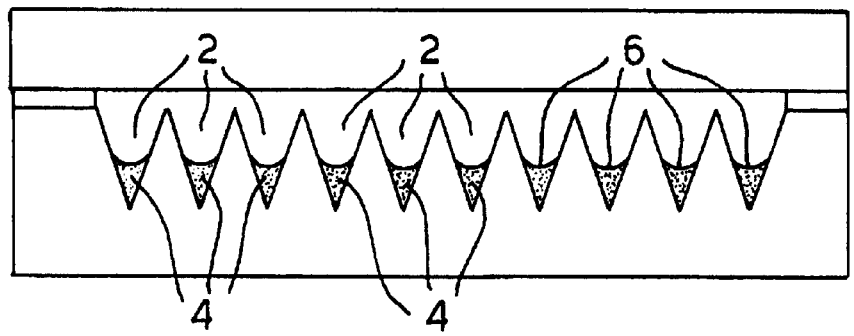
FIG. 5 is a cross sectional view of a fifth embodiment of the present invention.

Referring to FIG. 5, there is shown a modification of the embodiment of FIG. 3, where multiple apices 27 are formed to provide multiple channels for the first fluid, each apex 27 forming an open interface with the second fluid. This provides a means of producing systems with high fluid throughput.

As stated above, the present invention is applicable to the formation of an open interface maintained by surface tension, or to an interface maintained by a porous membrane between the fluids, as for example described in our copending International Application PCT/GB95/02488. In the latter case where a foraminated sheet is provided to define the interface, the dimensions of the apertures in the sheet may be varied along the length of the interface in addition to, or alternatively to, varying the dimensions of the channel or channels.

What is claimed is:

1. Apparatus for carrying out a process between first and second immiscible fluids, the apparatus comprising first and second channels constructed to define flow paths for permitting parallel and co-current fluid flow of respective first and second immiscible fluids therethrough while inhibiting mixing of the fluids, portions of the flow paths being disposed close to, or adjacent to, one another and communicating with one another to define a region in which, in use, a stable interface between the fluids is formed, further characterised in that one or more dimensions of the region is varied along the length of the interface in a direction of fluid flow to compensate for variation in the properties of the fluids during the carrying out of the process and thereby maintain stability of the interface.

2. Apparatus according to claim 1, wherein the cross sectional area of at least the first flow path is changed.

3. Apparatus according to claim 2, wherein the cross sectional area of at least the second flow path is changed.

4. Apparatus according to claim 2, wherein, in use, an open interface is formed between the flow paths and the height of the interface varies along the length of the interface in the direction of fluid flow.

5. Apparatus according to claim 2 wherein a foraminous sheet is provided to define the interface, and the dimensions of the apertures in the sheet vary along the length of the interface.

6. Apparatus according to claim 2 wherein at least at said region where the interface is formed, the first and second channels merge to form one or more tubes the, or each of which has two walls which converge in a direction extending normal to the interface to define a tapering cross section extending in a direction away from the interface to hold or trap the fluid therein.

7. Apparatus according to claim 1, wherein the cross sectional area of at least the second flow path is changed.

8. Apparatus according to claim 7, wherein, in use, an open interface is formed between the flow paths and the height of the interface varies along the length of the interface in the direction of fluid flow.

9. Apparatus according to claim 7 wherein a foraminous sheet is provided to define the interface, and the dimensions of the apertures in the sheet vary along the length of the interface.

10. Apparatus according to claim 7 wherein at least at said region where the interface is formed, the first and second channels merge to form one or more tubes the, or each of which has two walls which converge in a direction extending normal to the interface to define a tapering cross section extending in a direction away from the interface to hold or trap the fluid therein.

11. Apparatus according to claim 1, wherein, in use, an open interface is formed between the flow paths and the height of the interface varies along the length of the interface in the direction of fluid flow.

12. Apparatus according to claim 1, wherein a foraminous sheet is provided to define the interface, and the dimensions of apertures in the sheet vary along the length of the interface.

13. Apparatus according to claim 1 wherein at least at said region where the interface is formed, the first and second channels merge to form one or more tubes the, or each of which has two walls which converge in a direction extending normal to the interface to define a tapering cross section extending in a direction away from the interface to hold or trap the fluid therein.

14. Apparatus according to claim 13, wherein the channels merge at said region to form a tube of triangular cross sectional shape, with one apex of the triangle defining the first fluid flow path and a base of the triangular shape defining the second flow path.

15. Apparatus according to claim 13, wherein the channels merge at said region to form a tube having a cross sectional shape comprising a plurality of pairs of walls which converge mutually in a direction extending radially outwards relative to a central axis of the tube to form an apex, said apices defining the first fluid flow paths and the second flow paths being formed by a void extending along said central axis of the tube.

16. Apparatus according to claim 15 wherein the tube is of star shaped cross section.

17. Apparatus according to claim 1, wherein said flows paths for said first and second immiscible fluids are essentially laminar at said stable interface.

18. A method of carrying out a process between first and second immiscible fluids, the method comprising the acts of:

providing first and second channels defining flow paths for permitting fluid flow of respective first and second immiscible fluids therethrough, disposing portions of the flow paths close to, or adjacent to, one another and communicating with one another to define a region in which, in use, a stable interface between the fluids is formed, varying one or more dimensions of the region along the length of the interface in a direction of fluid flow to compensate for variation in the properties of the fluids during the carrying out of the process and thereby maintain stability of the interface.

* * * * *